United States Patent [19]

Ramirez et al.

[11] Patent Number: 5,346,307
[45] Date of Patent: Sep. 13, 1994

[54] USING ELECTRICAL RESISTANCE TOMOGRAPHY TO MAP SUBSURFACE TEMPERATURES

[75] Inventors: Abelardo L. Ramirez, Pleasanton; Dwayne A. Chesnut, San Francisco; William D. Daily, Livermore, all of Calif.

[73] Assignee: Regents of the University of California, Oakland, Calif.

[21] Appl. No.: 72,601

[22] Filed: Jun. 3, 1993

[51] Int. Cl.$^5$ .............. G01K 3/00; G01K 7/16; G01K 13/00
[52] U.S. Cl. .................. 374/136; 374/137; 374/166; 324/715
[58] Field of Search .............. 374/136, 137, 166, 183; 324/715, 718

[56] References Cited

U.S. PATENT DOCUMENTS

| | | | |
|---|---|---|---|
| 2,094,234 | 9/1937 | Drain, Jr. | 324/718 |
| 3,721,897 | 3/1973 | Edling | 324/715 |
| 4,656,595 | 4/1987 | Hognestad | 324/718 |
| 4,730,160 | 3/1988 | Cusack et al. | 374/44 |
| 4,737,917 | 4/1988 | Perron | 374/137 |
| 4,835,466 | 5/1989 | Maly et al. | 324/715 |
| 4,887,025 | 12/1989 | Re Fiorentin et al. | 324/718 |
| 4,916,715 | 4/1990 | Adiutori | 374/134 |
| 4,933,887 | 6/1990 | Danko et al. | 374/136 |
| 5,068,619 | 11/1991 | Nakano et al. | 324/715 |
| 5,165,794 | 11/1992 | Ortiz | 374/137 |

FOREIGN PATENT DOCUMENTS

| | | | |
|---|---|---|---|
| 0021882 | 2/1977 | Japan | 374/137 |
| 0265535 | 11/1987 | Japan | 374/137 |
| 0265537 | 11/1987 | Japan | 374/137 |
| 0083125 | 3/1989 | Japan | 374/137 |
| 0213579 | 8/1989 | Japan | 324/715 |
| 1402903 | 6/1988 | U.S.S.R. | 324/718 |

Primary Examiner—Diego F. F. Gutierrez
Attorney, Agent, or Firm—Henry P. Sartorio

[57] ABSTRACT

A method is provided for measuring subsurface soil or rock temperatures remotely using electrical resistivity tomography (ERT). Electrical resistivity measurements are made using electrodes implanted in boreholes driven into the soil and/or at the ground surface. The measurements are repeated as some process changes the temperatures of the soil mass/rock mass. Tomographs of electrical resistivity are calculated based on the measurements using Poisson's equation. Changes in the soil/rock resistivity can be related to changes in soil/rock temperatures when: (1) the electrical conductivity of the fluid trapped in the soil's pore space is low, (2) the soil/rock has a high cation exchange capacity and (3) the temperature changes are sufficiently high. When these three conditions exist the resistivity changes observed in the ERT tomographs can be directly attributed to changes in soil/rock temperatures. This method provides a way of mapping temperature changes in subsurface soils remotely. Distances over which the ERT method can be used to monitor changes in soil temperature range from tens to hundreds of meters from the electrode locations.

17 Claims, 1 Drawing Sheet

USING ELECTRICAL RESISTANCE TOMOGRAPHY TO MAP SUBSURFACE TEMPERATURES

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the use of electrical resistance tomography (ERT) to determine subsurface soil or rock temperatures. More specifically, it relates to a method for mapping temperature changes in subsurface soils through remote measurements.

2. Description of Related Art

Many applications require heating of subsurface soils or rocks. For example, steam injection can be used to heat soils and remove subsurface contaminants such as Volatile organic compounds. Steam injection is also used in oil reservoirs to enhance the recovery of petroleum. In both of these applications it is highly desirable to map the subsurface region through which steam has moved and to determine which regions have been bypassed by the steam. These processes can be made more cost-effective when the temperature distribution in the region of interest is known. Subsurface temperature measurements are generally made from boreholes using sensors which sample temperatures at a point along the borehole wall, however, these measurements only represent the temperature of the soil located within inches of the borehole. In order to measure temperatures at locations removed from one borehole requires drilling additional boreholes and the regions between boreholes cannot be measured. It would be beneficial to have a method which would minimize the need for and increase the utility of boreholes by providing means to monitor temperature changes remotely using electrodes located at the ground surface or in boreholes. The present invention provides such a method.

For a description of a simple physical model describing shaly sand conductivities, see M. H. Waxman et al., "Electrical Conductivities in Shaly Sands-I. The relation between hydrocarbon saturation and resistivity index; II. The temperature coefficient of electrical conductivity", *Journal of Petroleum Technology*, Vol. 26, pp. 213-218, 1974.

SUMMARY OF THE INVENTION

It is an object of the present invention to provide a method for remotely determining subsurface soil or rock temperatures using electrical resistance tomography.

A method is provided for determining subsurface soil or rock temperatures remotely using electrical resistivity tomography (ERT). Electrical resistivity measurements are made using electrodes either implanted in boreholes and/or emplaced at the ground surface. The measurements are repeated as some process changes the temperatures of the soil mass/rock mass. Tomographs of electrical resistivity are calculated based on the measurements. Changes in the soil/rock resistivity can be related to changes in soil/rock temperatures when the electrical conductivity of the fluid trapped in the soil's pore space is low, the soil/rock has a high cation exchange capacity and the temperature changes are sufficiently high. When these three conditions exist the resistivity changes observed in the ERT tomographs can be primarily attributed to changes in soil/rock temperatures. The method will provide the most accurate estimates when these three conditions are met. Decreasing accuracy occurs as the actual conditions deviate from those specified above. First, "before heating" and "during heating" tomographs are calculated; pixel by pixel intensity differences between the "before heating" and "during heating" tomographs are also calculated and difference tomographs generated. These difference tomographs show differences in resistivity which are then related to temperature changes. This method provides a way of mapping temperature changes in subsurface soils remotely. Distances over which the ERT method can be used to monitor changes in soil temperature range from tens to hundreds of meters from the electrode locations.

DETAILED DESCRIPTION OF THE INVENTION

Figure 1:
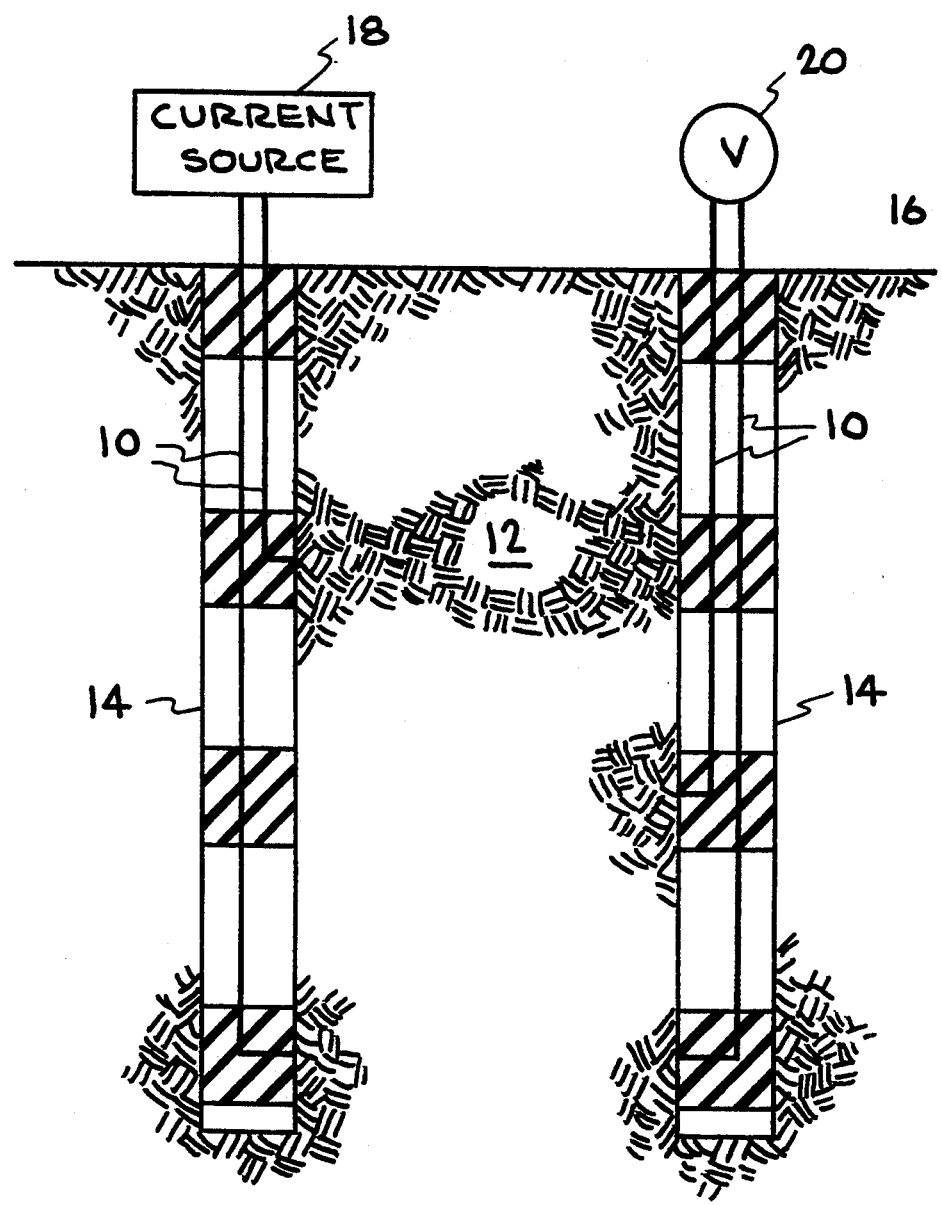
FIG. 1 illustrates a configuration for measuring resistivity between two boreholes.

This invention relates generally to the remote detection of subsurface temperature changes using a geophysical technique known as electrical resistivity tomography (ERT). To image the resistivity distribution between two boreholes, a number of electrodes are placed in electrical contact with the soil in each borehole and/or along the ground surface. Using an automatic data collection and switching system, a known current is applied to two electrodes and the resulting potential difference between other pairs of electrodes is measured. Each ratio of measured voltage and current is a transfer resistance. Next, current is applied between two other electrodes and the voltage differences are measured using electrode pairs not being used for the source current. This process is repeated until many combinations are measured.

Clay minerals in soils and rocks increase electrolytic conduction by adding pathways of electrical conductivity in addition to the path through electrolyte solution in the pore space. Clay particles possess a net negative charge which is compensated by an excess number of cations in solution close to clay surfaces. The cations/clay interface forms a "double layer" along which conduction occurs in addition to conduction through the electrolyte. This phenomenon tends to dominate any correlation between water saturation and resistivity when the resistivity of the groundwater is high and tile soil or rock cation exchange capacity is high. Decreasing accuracy occurs as the actual conditions deviate from those specified above.

Clay conductance contributes a significant fraction of total conductance under some conditions and modifies the saturation-porosity-water-resistivity relationship. The effects become more significant with increasing clay content, decreasing water saturation and increasing pore water resistivity and temperature. Decreases in bulk resistivity can be related to the effect of exchange cations on electrical conductivity as temperatures increase in the sediments. Using this relationship, measurements of bulk resistivity are used as an indicator of temperature exchanges in the sediments so long as: (1) the water resistivity is high, (2) the cation exchange capacity of the soil is high, and (3) the temperature changes are sufficiently high. This model is used to define the parameter ranges over which bulk resistivity can serve as an indicator of temperature changes.

The preferred embodiment of the present invention is a method for using ERT to map temperature changes in subsurface soil and rocks. Electrodes are emplaced at the ground surface and/or in boreholes such that the electrodes are in good electrical contact with the formation. One possible application of this approach is illustrated in FIG. 1. Electrode 10, placed in borehole 14 images plane 12 beneath surface 16 by measuring a potential difference at voltage meter 20, due to current injected at current source 18. Electrodes placed at the ground surface can be used when the region of interest is less than 30 meters deep. Measurements can also be made between electrodes in two boreholes or between the surface and borehole electrodes. FIG. 1 shows a configuration for measuring resistivity between two boreholes. Electrodes in each borehole make electrical contact with the formation.

A known current is applied to two or more electrodes and the resulting potential difference is measured between other pairs of electrodes. Next, a current is applied between two other electrodes and again, the voltage differences are measured using electrode pairs not being used for the source current. Each ratio of measured voltage and current is a transfer resistance. Optimally, this process is repeated until all the linearly independent combinations of measurements are measured. Usually, at least 100 data points are required. These measurements for a cross-borehole survey are similar to those used in a conventional surface dipole-dipole resistivity survey.

Soil/rock resistance is measured before a natural or man-made process causes temperature changes. Examples of such processes include: (1) injecting steam into the subsurface, (2) injecting current into the subsurface, (3) heating the subsurface with radio frequency waves, (4) heating the subsurface with warm water, and (5) heating the subsurface with geothermal processes. The measurements are repeated during and/or after the process changes the temperatures of the soil mass/rock mass. This measurement can be periodically made and can be accomplished with the same or different electrodes than that used to measure the soil/rock resistance before a process changes the subsurface temperature.

Tomographs of electrical resistivity (or electrical conductivity) are calculated using the resistance data collected. A tomography algorithm that solves Poisson's equation is used to translate the resistance data into a tomograph that shows the distribution of resistivities within the region of interest.

The "before heating" and "during heating" tomographs are used to calculate one or more difference tomographs. Pixel by pixel differences between the "before heating" and "during heating" tomographs are also calculated and difference tomographs generated. Other methods for producing these difference tomographs include calculating the percent difference of relative intensity between the tomographs produced "before heating" and "after heating", and calculating a ratio of intensity between the tomographs produced "before heating" and "after heating". These difference tomographs show differences in resistivity which are then related to temperature changes.

A model is used (for example, see Waxman supra) to relate the electrical conductivity of a soil/water or rock/water system to the pore water conductivity, temperature and the cation exchange capacities of the soil or rock. Derivations of the equations describing the model are used to calculate the temperature differences based on the electrical conductivity (or electrical resistivity) changes observed in the difference tomographs. Foe example, the general equation for the specific conductance of sand is $$C_o = 1/F^*(BQ_v + C_w),$$

where $1/F^*$ is the slope of the straight-line portion of the $C_o V_s C_w$ curve, $Q_v$ is the concentration of clay-exchange cations, $C_w$ is the specific conductance of the equilibrating brine, and B represents the equivalent conductance of the clay counterions as a function of $C_w$.

Electrical resistivity tomography (ERT) is a technique to reconstruct the distribution of resistivity inside a body from measurements of currents and voltages on its boundary. The method may be applied either to planar (two-dimensional) or to Volumetric (three-dimensional) imaging. Using a core sample to provide a two-dimensional example, a series of electrodes may be evenly spaced azimuthally around the core (W. D. Daily et al., "Hydrological Properties of Topopah Spring Tuff—Laboratory Measurements," *J. Geophysical Res.*, Vol. 92, pp. 7854–7864, 1987). Two adjacent electrodes are driven by a known current. The voltage difference between all other adjacent pairs of electrodes is measured. The transfer resistance is the ratio of that voltage and the current. Then, the known current is applied to two other adjacent electrodes and the voltage again measured between all other adjacent electrodes. This process is repeated until current has been applied to all pairs of adjacent electrodes. For n electrodes there will be $n(n-3)/2$ independent transfer resistances. This procedure is very similar to that used for dipole-dipole resistivity surveys. However, tomographic interpretation of these data is quite different from the traditional approaches.

One major difficulty with impedance imaging is in the reconstruction algorithm. It is necessarily much different from the algorithm used in x-ray tomography. In computerized tomography (CT) the x-rays, which are used for probing, travel in image-independent straight line paths. With ERT, the currents tend to flow along the paths of least resistance, and therefore are image dependent. This image dependency makes ERT a nonlinear reconstruction problem. The algorithm for CT depends on relatively simple back projection along the straight rays to deduce the attenuation coefficients giving rise to exponential decay of the x-rays along their paths. By contrast, impedance imaging requires the inversion of current and potential data using a fundamentally different approach.

The mathematical problem to be solved is Poisson's equation in the region of interest $$-\nabla \cdot (\sigma \nabla \phi) = 0 \qquad (1)$$

where $\nabla$ is the gradient operator and $\nabla \cdot$ is the divergence operator, $\sigma$ is the conductivity, $\phi$ is the electrical potential, and the solution to the equation is subject to Neumann boundary conditions on the surface $$\sigma(s)\eta \cdot \nabla \phi = j(s) \qquad (2)$$

where $\eta$ is the unit outward normal vector Equation (2) states that at active electrode sites, the surface current density is given by j(s), where j represents an impressed current source distribution on the boundary of the body of interest. Now, given multiple sets of measurements of $\phi$ and j, it is necessary to estimate the spatial variation of the conductivity $\sigma$. This mathematical problem has been studied by many people, for example, Dines and Lytle (K. A. Dines et al., "Analysis of Electrical Conductivity Imaging", Geophysics, Vol. 46, pp. 1025-1026, 1981) used circuit analysis to generate estimates of the conductivity using an iterative process on network equations that are linearized in the unknown conductance variables. Although this approach is successful in some situations, convergence can be quite slow. Also, there is no guarantee of convergence if the initial guess of the conductivity distribution is so inaccurate that the required linearization provides poor estimates of succeeding increments in the local conductivity. Subsequent to this early work, many have tried other approaches with varying degrees of success (e.g., R. Henderson et al., "An Impedance Camera for Spatially Specific Measurements of the Thorax", *IEEE Trans. Biomech. Eng. BME*, Vol. 25, pp. 250-254, 1978). T. J. Yorkey, "Comparing Reconstruction Methods for Electrical Impedance Tomography", Ph. D. Thesis, Dept. of Elect. Comp. Eng., Univ. of Wisconsin, Madison, Wis. 53706, August 1986, has developed a finite element algorithm and has shown it to be superior to the previous algorithms.

Inversion schemes require linearization of the governing equations and this process tends to make them unstable, especially in the presence of data noise. A fundamentally new approach to stabilizing the inversion algorithms has recently been developed (see J. G. Berryman, "Convexity Properties of Inverse Problems with Variational Constraints", *J. Franklin Inst.*, Vol. 328, pp. 1–13, 1991). This approach constrains the solution to lie in the physically realizable regions of the model space—thus the constraints are called feasibility constraints, for example, to invert electrical boundary measurements to obtain the interior conductivity distribution of a body. Then the set of powers (dissipated while current is injected between pairs i of electrodes $\{P_i\}$) is the pertinent data set to define a feasibility boundary.

Changes and modifications in the specifically described embodiments can be carried out without departing from the scope of the invention, which is intended to be limited by the scope of the appended claims.

We claim:

1. A method for remotely determining subsurface soil or rock temperatures using electrical resistance tomography, comprising:
   a. measuring subsurface soil or rock ground resistance at least twice with a set of electrodes;
   b. calculating an electrical resistance tomograph using Poisson's equation from the measured ground resistances;
   c. re-measuring the subsurface soil or rock ground resistances as a process changes the temperature of the subsurface soil or rock;
   d. calculating an electrical resistance tomograph from the re-measured ground resistances using said Poisson's equation;
   e. calculating a difference tomograph from the tomographs produced from the measuring and the re-measuring steps; and
   f. relating said difference tomograph to changes in soil or rock temperature.

2. The method of claim 1, wherein step (a) is carried out with electrodes implanted in boreholes.

3. The method of claim 1, wherein step (a) is carried out with electrodes emplaced on the surface of the ground.

4. The method of claim 1, wherein step (a) is carried out with electrodes implanted in boreholes and emplaced on the surface of the ground.

5. The method of claim 1, wherein the step (c) is carried out periodically.

6. The method of claim 1, wherein the process in step (c) is carried out by injecting steam into the subsurface.

7. The method of claim 1, wherein the process in step (c) is carried out by injecting current into the subsurface.

8. The method of claim 1, wherein the process in step (c) is carried out by heating the subsurface with radio frequency waves.

9. The method of claim 1, wherein the process in step (c) is carried out by heating the subsurface with warm water.

10. The method of claim 1, wherein step (c) is carried out with the same set of electrodes as the set of electrodes used in step (a).

11. The method of claim 1, wherein step (c) is carried out with a different set of electrodes than the set of electrodes used in step (a).

12. The method of claim 1, wherein step (e) is carried out by calculating the pixel by pixel intensity difference of the tomographs produced in steps (b) and (d), to show the resistivity difference.

13. The method of claim 1, wherein step (e) is carried out by calculating the percent difference of relative intensity between the tomographs produced in steps (b) and (d), to show the resistivity difference.

14. The method of claim 1, wherein step (e) is carried out by calculating a ratio of intensity between the tomographs produced in steps (b) and (d), to show the resistivity difference.

15. The method of claim 1, wherein step (f) is carried out by using a model that relates the electrical resistivity of a soil/water or rock/water system to the pore water resistivity, temperature and the cation exchange capacities of the soil or rock.

16. A method for remotely determining subsurface soil or rock temperatures using electrical resistance tomography, comprising:
   a. measuring subsurface soil or rock ground resistance at least twice;
   b. calculating an electrical resistance tomograph using Poisson's equation from the measured ground resistances;
   c. re-measuring the subsurface soil or rock ground resistances after a process changes the temperature of the subsurface soil or rock;
   d. calculating an electrical resistance tomograph from the re-measured ground resistances using said Poisson's equation;
   e. calculating a difference tomograph from the tomographs produced from the measuring and the re-measuring steps; and
   f. relating said difference tomograph to changes in soil or rock temperature.

17. A method for remotely determining subsurface soil or rock temperatures using electrical resistance tomography, comprising:

a. measuring subsurface soil or rock ground resistance at least twice;
b. calculating an electrical resistance tomograph using Poisson's equation from the measured ground resistances;
c. re-measuring the subsurface soil or rock ground resistances during and after a process changes the temperature of the subsurface soil or rock;
d. calculating an electrical resistance tomograph from the re-measured ground resistances using said Poisson's equation;
e. calculating a difference tomograph from the tomographs produced from the measuring and the re-measuring steps; and
f. relating said difference tomograph to changes in soil or rock temperature.

* * * * *